(12) United States Patent
Qi et al.

(10) Patent No.: US 12,262,704 B2
(45) Date of Patent: Apr. 1, 2025

(54) EASY-TO-CLEAN VISUAL GRAIN MONITORING DEVICE

(71) Applicant: CHENGDU AUTO SENSOR TECHNOLOGY CO.LTD, Sichuan (CN)

(72) Inventors: Xiaochun Qi, Sichuan (CN); Tao Li, Sichuan (CN); Xin Li, Sichuan (CN); Ou Bai, Sichuan (CN); Fuzhi Huang, Sichuan (CN); Zhuzhi Ye, Sichuan (CN); Li Sang, Sichuan (CN)

(73) Assignee: CHENGDU AUTO SENSOR TECHNOLOGY CO.LTD, Chengdu (CN)

( * ) Notice: Subject to any disclaimer, the term of this patent is extended or adjusted under 35 U.S.C. 154(b) by 406 days.

(21) Appl. No.: 17/791,538

(22) PCT Filed: Apr. 27, 2021

(86) PCT No.: PCT/CN2021/090229
§ 371 (c)(1),
(2) Date: Jul. 8, 2022

(87) PCT Pub. No.: WO2022/041814
PCT Pub. Date: Mar. 3, 2022

(65) Prior Publication Data
US 2023/0029527 A1    Feb. 2, 2023

(30) Foreign Application Priority Data

Aug. 31, 2020 (CN) .................. 202010897815.X
Aug. 31, 2020 (CN) .................. 202021868934.4
(Continued)

(51) Int. Cl.
*A01M 1/02* (2006.01)
*G01N 33/02* (2006.01)
(Continued)

(52) U.S. Cl.
CPC ............. *A01M 1/026* (2013.01); *G01N 33/02* (2013.01); *H04N 7/183* (2013.01); *A01M 1/00* (2013.01); *A01M 5/00* (2013.01)

(58) Field of Classification Search
CPC .......... A01M 1/026; A01M 1/00; A01M 5/00; A01M 1/103; A01M 17/008; A01M 23/08;
(Continued)

(56) References Cited

U.S. PATENT DOCUMENTS

| 5,646,404 A * | 7/1997 | Litzkow ................ A01M 1/026 250/358.1 |
| 2008/0181352 A1* | 7/2008 | Hirafuji ................ A01M 1/223 377/16 |
| 2021/0153492 A1* | 5/2021 | Chang .................... A01M 1/04 |

\* cited by examiner

*Primary Examiner* — Alazar Tilahun
(74) *Attorney, Agent, or Firm* — Bayramoglu Law Offices LLC

(57) ABSTRACT

An easy-to-clean visual grain monitoring device includes a housing. A circuit board is provided within the housing and is connected with a monitoring unit; an insect collecting pipe, which is provided within the housing, includes multiple first entrances; the housing includes multiple second entrances which are corresponding to the first entrances respectively; an execution element, which is installed on a base, is connected with a lower end of the insect collecting pipe for driving the insect collecting pipe to move up and down; an insect leaking passage, which is provided at an upper end of the base, extends downwards along a side wall of the base; a tail end of the insect leaking passage has a first insect leaking hole for discharging pests, the housing has a second insect leaking hole in a position corresponding to the first insect leaking hole.

9 Claims, 6 Drawing Sheets

(30)  Foreign Application Priority Data

Mar. 30, 2021 (CN) .......................... 202110339310.6
Mar. 30, 2021 (CN) .......................... 202120648519.6

(51) Int. Cl.
*H04N 7/18* (2006.01)
*A01M 1/00* (2006.01)
*A01M 5/00* (2006.01)

(58) Field of Classification Search
CPC ........ G01N 33/02; G01N 21/84; H04N 7/183;
G01D 21/02
See application file for complete search history.

EASY-TO-CLEAN VISUAL GRAIN MONITORING DEVICE

CROSS REFERENCE OF RELATED APPLICATION

This is a U.S. National Stage under 35 U.S.C 371 of the International Application PCT/CN2021/090229, filed Apr. 27, 2021, which claims priority under 35 U.S.C. 119(a-d) to CN 202010897815.X, filed Aug. 31, 2020, CN 202021868934.4, filed Aug. 31, 2020, CN 202110339310.6, filed Mar. 30, 2021 and CN 202120648519.6, filed Mar. 30, 2021.

BACKGROUND OF THE PRESENT INVENTION

Field of Invention

The present invention relates to the field of grain environmental monitoring, and more particularly to an easy-to-clean visual grain monitoring device.

Description of Related Arts

There is a Chinese saying that "hunger breeds discontentment". Grain is vital to people's survival. China is a country with a large population and consumes a large amount of grain every year, so it is very important to store grain. If grain storage is not managed properly, the grain will suffer from pests and mildew, causing the grain is inedible or even is unable to be sown as seed. According to relevant statistics, the annual loss of grain in China is as high as 100 million RMB. Therefore, it is particularly important to manage the grain storage.

During storage, effective measures are required to monitor the temperature, humidity, insect pests and other conditions of grains, so as to respond to manage situations in a timely manner. At the same time, intelligent and precise monitoring methods are also required to provide accurate data for grain management personnel and give rationalized treatment opinions, reducing manpower and material resources.

Chinese Application No. CN 202011421517.X, titled as "visual grain monitoring device", discloses a grain monitoring device. However, in the technical solution disclosed in the patent application, if the pests stored in the inner casing need to be cleaned up, the outer casing and the inner casing need to be completely removed, so that the cleaning process is quite troublesome. Moreover, improper remove operation may cause damage to the internal structure of the grain monitoring device.

SUMMARY OF THE PRESENT INVENTION

Aiming at the problem that while being cleaned, the existing grain monitoring device needs to be completely disassembled, the present invention provides an easy-to-clean visual grain monitoring device.

The present invention provides technical solutions as follows.

An easy-to-clean visual grain monitoring device comprises a housing, wherein:
a circuit board is provided within the housing and is connected with a monitoring unit;
an insect collecting pipe, which is provided within the housing, comprises multiple first entrances; the housing comprises multiple second entrances which are corresponding to the first entrances respectively;
an execution element, which is installed on a base, is connected with a lower end of the insect collecting pipe for driving the insect collecting pipe to move up and down;
an insect leaking passage, which is provided at an upper end of the base, extends downwards along a side wall of the base;
a tail end of the insect leaking passage has a first insect leaking hole for discharging pests, the housing has a second insect leaking hole in a position corresponding to the first insect leaking hole, and the lower end of the insect collecting pipe has a third insect leaking hole staggered with the insect leaking passage.

Preferably, an upper end and a lower end of the housing has two openings respectively, two end plugs are provided at the upper and lower ends of the housing for sealing and are connected with the housing through two location pins respectively; the two end plugs have two connecting holes respectively; the monitoring unit comprises a camera, a temperature sensor and a humidity sensor; a fill-in light is provided beside the camera; the insect collecting pipe is provided at an area which is illuminated by the camera.

Preferably, the execution element is installed on the base; a connecting rod, which is provided at the lower end of the insect collecting pipe near the base, is connected with an output end of the execution element; one end of the base near the insect collecting pipe has a mounting hole; the connecting rod and the output end of the execution element define a whole which is able to slide within the mounting hole.

Preferably, the insect leaking passage, which is provided outside the mounting hole, extends downwards along the side wall of the base; the tail end of the insect leaking passage has the first insect leaking hole for discharging the pests; the housing has the second insect leaking hole in the position corresponding to the first insect leaking hole; the lower end of the insect collecting pipe has the third insect leaking hole staggered with the insect leaking passage, wherein when the lower end of the insect collecting pipe is completely fitted with the base, the third insect leaking hole is blocked by the base, and at this time, the lower end of the insect collecting pipe and the base form a complete bottom surface, the insect leaking passage is blocked; when the execution element drives the insect collecting pipe to move upwards, the lower end of the insect collecting pipe is away from the base, so that a gap is formed between the insect collecting pipe and the base; and at the same time, the insect leaking passage is unblocked, the third insect leaking hole is unblocked.

Preferably, the base has a mounting slot for accommodating the execution element; a movement slot for accommodating the output end of the execution element is provided above the mounting slot; the mounting hole is provided above the movement slot; the connecting rod passes through the mounting hole and is connected with the output end of the execution element.

Preferably, two insect leaking passages are provided at two sides of the mounting hole, an upper end of the insect leaking passages and the mounting hole define a cuboid space; a strip, which matches the cuboid space, is provided at the lower end of the insect collecting pipe and is connected with the connecting rod; the third insect leaking hole is provided at the lower end of the insect collecting pipe where is not blocked by the strip.

Preferably, the first insect leaking holes are defined by two wedge-shaped grooves at two sides of the base and the housing sleeved on the base respectively; two head ends of the wedge-shaped grooves are communicated with the insect leaking passages, and two pointed ends of the wedge-shaped grooves are aligned with the second insect leaking holes respectively.

Preferably, a circular insect leaking passage is provided outside the mounting hole; a round baffle is provided on the insect collecting pipe through a bracket at a position corresponding to the circular insect leaking passage; the round baffle has the same size as the insect leaking passage; the connecting rod is provided at a center of the round baffle; the lower end of the insect collecting pipe that is not covered by the round baffle defines the third insect leaking hole; an upper portion of the insect leaking passage is inclined.

Preferably, the insect collecting pipe has two sliding slots at two sides thereof for limiting position, two support frames for cooperating with the sliding slots are provided on the base, and the support frames are engaged with the sliding slots respectively.

Preferably, a sealed cabin is sleeved on the circuit board for sealing, two assembly bumps for connecting with the support frames respectively are provided at a lower portion of the sealed cabin, the two support frames have two assembly holes at an upper portion thereof respectively for cooperating with the two assembly bumps, the support frames are connected with the sealed cabin through inserting the assembly bumps into the assembly holes respectively, a length of the support frames is larger than a length of the insect collecting pipe.

Preferably, the camera is set at a bottom of the circuit board and is opposite to the insect collecting pipe, a bottom surface of the sealed cabin is made from transparent materials, a sealing plug is provided above the circuit board and within the sealed cabin and has reserved holes for allowing pins of the temperature sensor and the humidity sensor to pass through.

Preferably, a wireless transmission module is provided within the circuit board.

Also, the present invention provides a monitoring system which comprises multiple easy-to-clean visual grain monitoring devices connected with each other through multiple cable units, wherein each of the cable units comprises a steel cable for withstanding external forces and a signal wire for signal transmission; two ends of the steel cable of the each of the cable units are connected with a location pin which is located at a lower end of a housing of an upper one of two adjacent visual grain monitoring devices, and a location pin which is located at an upper end of a housing of a lower one of the two adjacent visual grain monitoring devices, respectively.

Also, the present invention provides a monitoring system which comprises multiple easy-to-clean visual grain monitoring devices connected with each other through multiple cable units, wherein each of the cable units comprises a steel cable for withstanding external forces; two ends of the steel cable of the each of the cable units are connected with a location pin which is located at a lower end of a housing of an upper one of two adjacent visual grain monitoring devices, and a location pin which is located at an upper end of a housing of a lower one of the two adjacent visual grain monitoring devices, respectively.

Compared with prior arts, the present invention has some beneficial effects as follows.

(1) An easy-to-clean visual grain monitoring device comprises a housing, wherein a circuit board is provided within the housing and is connected with a monitoring unit; an insect collecting pipe, which is provided within the housing, comprises multiple first entrances; the housing comprises multiple second entrances which are corresponding to the first entrances respectively; an execution element, which is installed on a base, is connected with a lower end of the insect collecting pipe for driving the insect collecting pipe to move up and down; an insect leaking passage, which is provided at an upper end of the base, extends downwards along a side wall of the base; a tail end of the insect leaking passage has a first insect leaking hole for discharging pests, the housing has a second insect leaking hole in the position corresponding to the first insect leaking hole, and the lower end of the insect collecting pipe has a third insect leaking hole staggered with the insect leaking passage. When the lower end of the insect collecting pipe is completely fitted with the base, the third insect leaking hole is blocked by the base, and at this time, the lower end of the insect collecting pipe and the base form a complete bottom surface, the insect leaking passage is blocked and the pests in the insect collecting pipe are unable to be discharged from the insect leaking passage. When the execution element drives the insect collecting pipe to move upwards, the lower end of the insect collecting pipe is away from the base, so that a gap is formed between the insect collecting pipe and the base; and at the same time, the insect leaking passage is unblocked, the third insect leaking hole is also unblocked, and the pests are able to be discharged through the third insect leaking hole, and then enter the insect leaking passage through the gap between the insect collecting pipe and the base, and then move downwards through the insect leaking passage and reach the first insect leaking hole, and then are discharged through the second insect leaking hole of the housing via the first insect leaking hole, thereby achieving cleaning. The cleaning process is convenient.

(2) In the easy-to-clean visual grain monitoring device, the insect collecting pipe has two sliding slots at two sides thereof for limiting position, two support frames for cooperating with the sliding slots are provided on the base, and the support frames are engaged with the sliding slots respectively; the support frames are engaged with the sliding slots respectively for further limiting the movement direction of the insect collecting pipe, thereby providing better protection.

(3) In the easy-to-clean visual grain monitoring device, the sealed cabin is sleeved on the circuit board for sealing, two assembly bumps for connecting with the support frames respectively are provided at a lower portion of the sealed cabin, the two support frames have two assembly holes at an upper portion thereof respectively for cooperating with the two assembly bumps, the support frames are connected with the sealed cabin through inserting the assembly bumps into the assembly holes respectively, a length of the support frames is larger than a length of the insect collecting pipe; the assembly bumps are cooperated with the assembly holes to connect and fix the circuit board, the insect collecting pipe and the base. The monitoring device is simple in structure and strong in stability.

(4) A monitoring system comprises multiple easy-to-clean visual grain monitoring devices connected with each other through multiple cable units. Every two adjacent visual grain monitoring devices are connected with each other through one cable unit, wherein two ends of the steel cable of the one cable unit are connected with a location pin which is located at a lower end of a housing of an upper one of the two adjacent visual grain monitoring devices, and a location pin which is located at an upper end of a housing of a lower one of the two adjacent visual grain monitoring devices and so on, thereby obtaining the monitoring system. In this way, monitoring systems with different lengths are able to be selected according to the needs of customers and the corresponding use environment. The length of the monitoring system depends on the gap between the two adjacent visual grain monitoring devices and the total number of the monitoring devices.

(5) A monitoring system comprises multiple easy-to-clean visual grain monitoring devices connected with each other through multiple cable units. Every two adjacent visual grain monitoring devices are connected with each other through one cable unit, wherein two ends of the steel cable of the one cable unit are connected with a location pin which is located at a lower end of a housing of an upper one of the two adjacent visual grain monitoring devices, and a location pin which is located at an upper end of a housing of a lower one of the two adjacent visual grain monitoring devices. The signals are sent by the wireless transmission module, which is provided within the circuit board for signal transmission, and then are received by the external processing device, so that the connection without signal wires between the monitoring devices is able to be realized, which completely avoids the signal wire breakage due to pulling during the placement and removal of the monitoring system, thus affecting the signal transmission.

(6) In the easy-to-clean visual grain monitoring device, a circular insect leaking passage is provided outside the mounting hole; a round baffle is provided on the insect collecting pipe through a bracket at a position corresponding to the circular insect leaking passage; the round baffle has the same size as the insect leaking passage; the connecting rod is provided at a center of the round baffle; the lower end of the insect collecting pipe that is not covered by the round baffle defines the third insect leaking hole; an upper portion of the insect leaking passage is inclined. The bracket and the round baffle are able to increase an area of the third insect leaking hole to the greatest extent, so as to achieve the effect of quick cleaning. The upper portion of the insect leaking passage is inclined, so that the insects slide down directly to the first insect leaking hole under the action of gravity, thus the cleaning is done more cleanly.

Figure 1:
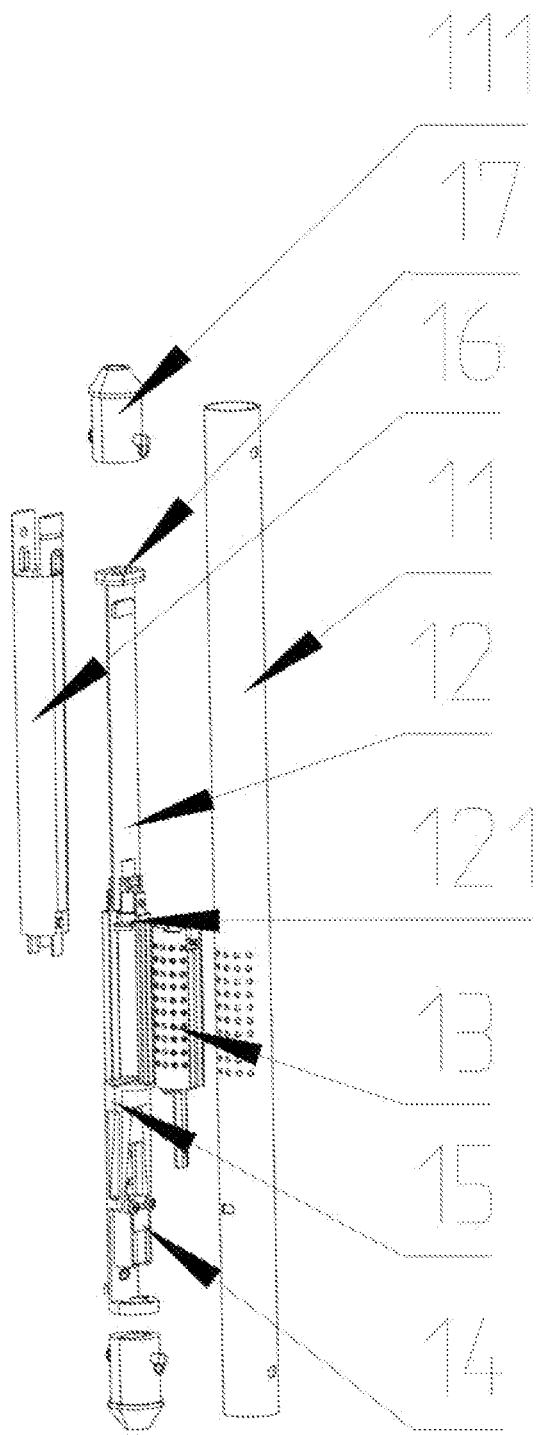
FIG. 1 is a structural schematic diagram of an easy-to-clean visual grain monitoring device provided by the present invention.
Figure 2:
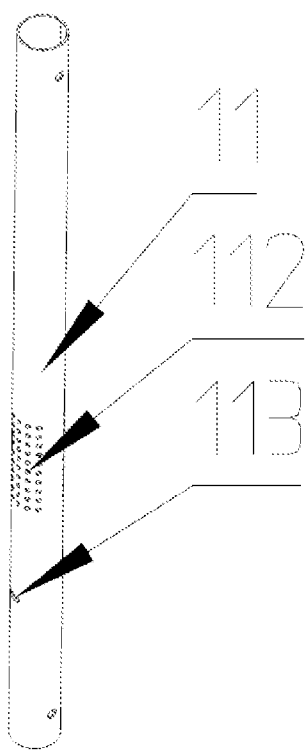
FIG. 2 is a structural schematic diagram of a housing of the easy-to-clean visual grain monitoring device provided by the present invention.
Figure 3:
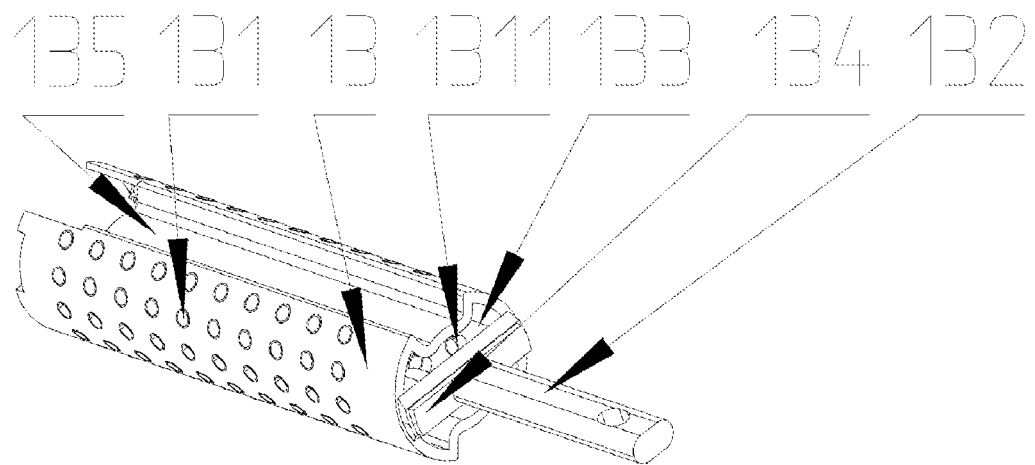
FIG. 3 is a structural schematic diagram of an insect collecting pipe of the easy-to-clean visual grain monitoring device provided by the present invention.
Figure 4:
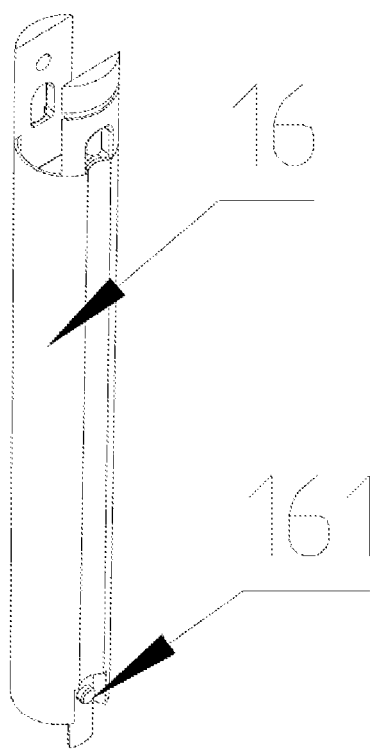
FIG. 4 is a structural schematic diagram of a sealed cabin of the easy-to-clean visual grain monitoring device provided by the present invention.
Figure 5:
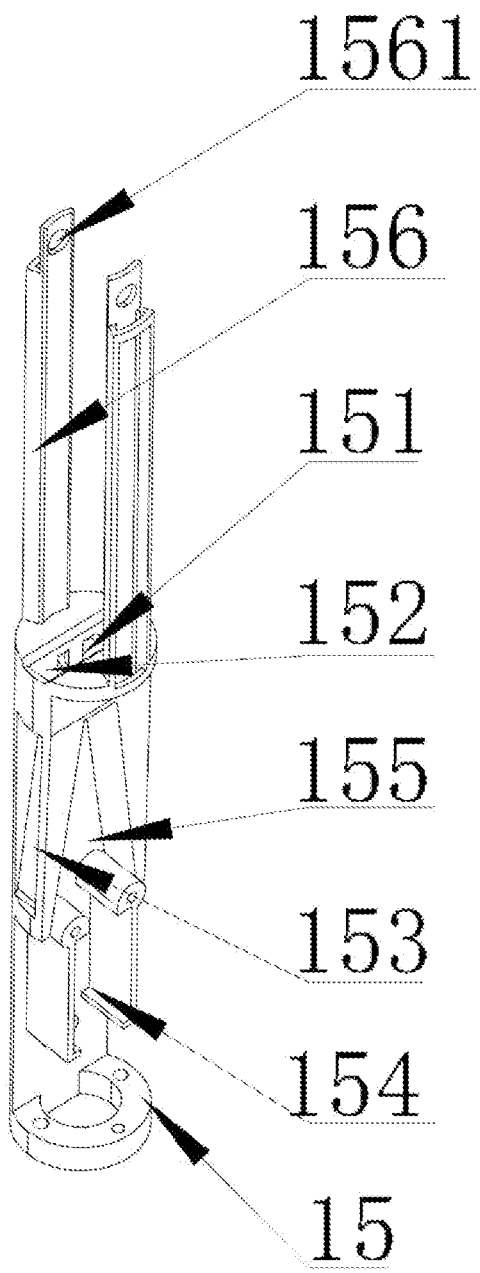
FIG. 5 is a structural schematic diagram of a base of the easy-to-clean visual grain monitoring device provided by the present invention.
Figure 6:
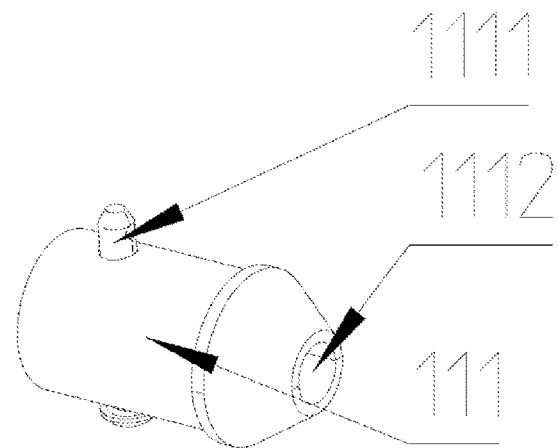
FIG. 6 is a structural schematic diagram of an end plug of the easy-to-clean visual grain monitoring device provided by the present invention.
Figure 7:
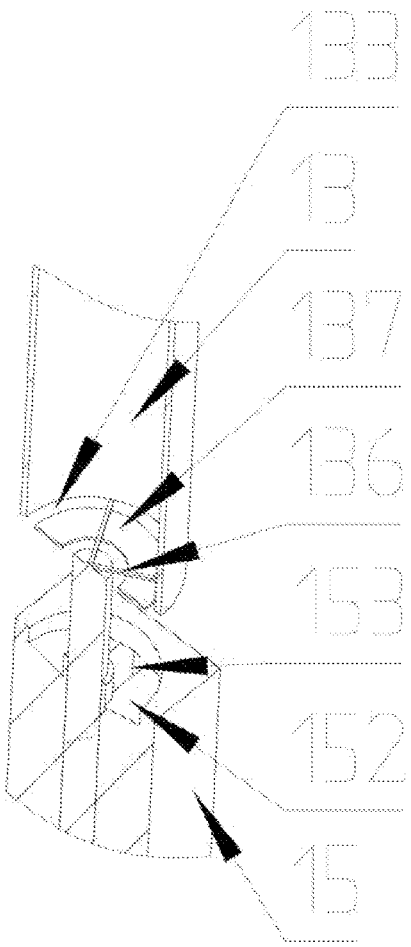
FIG. 7 shows the connection between the insect collecting pipe and the base according to the fifth embodiment of the present invention.

In the drawings, 1: easy-to-clean visual grain monitoring device; 2: steel cable; 3: signal wire; 11: housing; 12: circuit board; 13: insect collecting pipe; 14: execution element; 15: base; 16: sealed cabin; 17: sealing plug; 111: end plug; 112: second entrance; 113: second insect leaking hole; 121: camera; 131: first entrance; 132: connecting rod; 133: third insect leaking hole; 134: strip; 135: sliding slot; 136: bracket; 137: round baffle; 151: mounting hole; 152: insect leaking passage; 153: first insect leaking hole; 154: mounting slot; 155: movement slot; 156: support frame; 161: assembly bump; 1111: location pin; 1112: connecting hole; 1311: protuberance; 1561: assembly hole.

DETAILED DESCRIPTION OF THE PREFERRED EMBODIMENT

It should be noted that relational terms such as "first" and "second" are only used to distinguish one entity or operation from another entity or operation, and do not necessarily require or imply any actual relationship or ordering among these entities or operations.

The characteristics and performances of the present invention will be further described in detail in combination with the embodiments as follows.

First Embodiment

Referring to FIGS. 1-6, an easy-to-clean visual grain monitoring device according to a first embodiment of the present invention is illustrated, which comprises a housing 11. Preferably, the housing 11 is embodied as a cylindrical stainless steel pipe. Two ends of the housing 11 has two openings respectively, two end plugs 111 are provided at the two ends of the housing 11 for sealing and are connected with the housing 11 through two location pins 1111 respectively. The two end plugs 111 have two connecting holes 1112 respectively. A circuit board 12 is provided within the housing 11 for core control, and multiple electrical components are welded on the circuit board 12. The circuit board 12 is connected with a monitoring unit. The monitoring unit comprises a camera 121, a temperature sensor and a humidity sensor. A fill-in light is provided beside the camera 121. An insect collecting pipe 13 for storing pests is provided at an area which is illuminated by the camera 121. The insect collecting pipe 13 comprises multiple first entrances 131 for entry of the pests. Multiple protuberances 1311 are provided at an inner wall of the first entrances 131 respectively, so that after climbing into the insect collecting pipe 13 from the grain through the first entrances 131, the insects fall directly from an edge of the protuberances 1311 to a bottom of the insect collecting pipe 13 under an action of gravity. Moreover, due to the protuberances 1311, the pests are not easy to escape after entering the insect collecting pipe 13, which reduces the chance of missing shots. The housing 11 comprises multiple second entrances 112 which are corresponding to the first entrances 131 respectively for the entry of the pests. The pests enter the insect collecting pipe 13 through the second entrances 112 and the first entrances 131 in sequence. The camera 121 is configured to collect image information in the insect collecting pipe 13.

An execution element 14 for moving the insect collecting pipe 13 up and down is connected with a lower end of the insect collecting pipe 13. The circuit board 12 is connected with the execution element 14 for controlling the execution element 14 to work. The insect collecting pipe 13 moves up and down relatively to the housing 11, so that the first entrances 131 of the insect collecting pipe 13 are misaligned with the second entrances 112 of the housing 11. When the easy-to-clean visual grain monitoring device monitors, the execution element 14 drive the insect collecting pipe 13 to move to align the first entrances 131 with the second entrances 112, and at this time, the pests are able to smoothly enter the insect collecting pipe 13 through the second entrances 112 and the first entrances 131 in sequence, thereby achieving monitoring.

The execution element 14 is installed on the base 15. The base 15 is fixed with the housing 11 through bolts. A connecting rod 132 is provided at a lower end of the insect collecting pipe 13 near the base 15, and is connected with an output end of the execution element 14. The output end of the execution element 14 stretches up and down to drive the insect collecting pipe 13 to move up and down. One end of the base 15 near the insect collecting pipe 13 has a mounting hole 151. The connecting rod 132 and the output end of the execution element 14 define a whole which is able to slide within the mounting hole 151. The mounting hole 151 is configured to limit the deflection of the insect collecting pipe 13 when the insect collecting pipe 13 moves up and down.

Two insect leaking passages 152 are provided outside the mounting hole 151. The insect leaking passages 152 extend downwards along a side wall of the base 15, and two tail ends of the insect leaking passages 152 have two first insect leaking holes 153 for discharging the insects respectively. The housing 11 has two second insect leaking holes 113 in positions corresponding to the first insect leaking holes 153 respectively. The lower end of the insect collecting pipe 13 has a third insect leaking hole 133 staggered with the insect leaking passages 152. When the lower end of the insect collecting pipe 13 is completely fitted with the base 15, the third insect leaking hole 133 is blocked by the base 15, and at this time, the lower end of the insect collecting pipe 13 and the base form a complete bottom surface, the insect leaking passages 152 are blocked, so that the pests located in the insect collecting pipe 13 are unable to be discharged from the insect leaking passages 152. When the execution element 14 drives the insect collecting pipe 13 to move upwards, the lower end of the insect collecting pipe 13 is away from the base 15, so that a gap is formed between the insect collecting pipe 13 and the base 15; and at the same time, the insect leaking passages 152 are unblocked, the third insect leaking hole 133 is also unblocked, the insects are able to be discharged through the third insect leaking hole 133, and then enter the insect leaking passages 152 through the gap between the insect collecting pipe 13 and the base 15, and then move downwards through the insect leaking passages 152 and reach the first insect leaking holes 153, and then are discharged through the second insect leaking holes 113 of the housing 11 via the first insect leaking holes 153 respectively, thereby achieving cleaning.

Second Embodiment

The second embodiment is a further description of the first embodiment, and the same components are not repeated here. Referring to FIGS. 1-6, the base 15 is cylindrical, a diameter of the base 15 is slightly smaller than an inner diameter of the housing 11, and an assembly gap of 0.5 mm is reserved between the base 15 and the housing 11 in the design. The execution element 14 is able to be a telescopic motor or an electric actuator. According to the second embodiment of the present invention, the execution element 14 is embodied as the telescopic motor. The base 15 has a mounting slot 154 for accommodating the execution element 14. A movement slot 155 for accommodating the output end of the execution element 14 is provided above the mounting slot 154. The mounting hole 151 is provided above the movement slot 155. The connecting rod 132 passes through the mounting hole 151 and is connected with the output end of the execution element 14 in a plugged manner.

Two insect leaking passages 152 are provided at two sides of the mounting hole 151, that is, an upper end of the insect leaking passages 152 and the mounting hole 151 are provided at a same plane, and the upper end of the insect leaking passages 152 and the mounting hole 151 define a cuboid space. A strip 134, which matches the cuboid space, is provided at the lower end of the insect collecting pipe 13 and is connected with the connecting rod 132. The third insect leaking hole 133 is provided at the lower end of the insect collecting pipe 13 where is not blocked by the strip 134. When the execution element 14 drives the insect collecting pipe 13 to move downwards, the lower end of the insect collecting pipe 13 closely contacts with the base 15, the strip 134 closely contacts with the space formed by the insect leaking passages 152 and the mounting hole 151, the third insect leaking hole 133 is block by the base 15, and at this time, the lower end of the insect collecting pipe 13 and the base 15 form the complete bottom surface, thereby achieving sealing.

The first insect leaking holes 153 are defined by two wedge-shaped grooves at two sides of the base 15 and the housing 11 sleeved on the base 15 respectively. Two head ends of the wedge-shaped grooves are communicated with the insect leaking passages 152, and two pointed ends of the wedge-shaped grooves are aligned with the second insect leaking holes 113 respectively. When the execution element 14 drives the insect collecting pipe 13 to move upwards, the third insect leaking hole 133 is unblocked, the insects are discharged from the third insect leaking hole 133, and then enter the first insect leaking holes 153 through the insect leaking passages 152, and then fall to a bottom (i.e., the pointed ends of the wedge-shaped grooves) of the first insect leaking holes 153 under the action of gravity, and then are discharged through the second insect leaking holes 113.

Third Embodiment

The third embodiment is a further improvement to the second embodiment, and the same components are not repeated here. Referring to FIGS. 1-6, the insect collecting pipe 13 is also cylindrical, a diameter thereof is slightly smaller than an inner diameter of the housing 11, and an assembly gap of 0.5 mm is reserved between the insect collecting pipe 13 and the housing 11. The insect collecting pipe 13 for limiting position has two sliding slots 135 at two sides thereof respectively. Two support frames 156 for cooperating with the sliding slots 135 are provided on the base 15. After installation, the support frames 156 are engaged with the sliding slots 135 respectively for further defining a movement direction of the insect collecting pipe 13.

Since the insect collecting pipe 13 is also cylindrical, a diameter of the insect collecting pipe 13 is slightly smaller than the inner diameter of the housing 11. When the insect collecting pipe 13 is away from the base 15, the lower end of the insect collecting pipe 13 and the base 15 form a sealed space for ensuring that all the insects in the insect collecting pipe 13 are able to be discharged and are not get stuck in the insect collecting pipe 13.

Fourth Embodiment

The fourth embodiment is a further improvement to the third embodiment, and the same components are not repeated here. Referring to FIGS. 1-6, a cylindrical sealed cabin 16 is sleeved on the circuit board 12 for sealing, a diameter of the sealed cabin 16 is slightly smaller than the inner diameter of the housing 11, and an assembly gap of 0.5 mm is reserved between the sealed cabin 16 and the housing 11. The sealed cabin 16 is fixed with the housing 11 through bolts. Two assembly bumps 161 for connecting with the support frames 156 respectively are provided at a lower portion of the sealed cabin 16. The two support frames 156 have two assembly holes 1561 at an upper portion thereof respectively for cooperating with the two assembly bumps 161. The support frames 156 are relatively long, and preferably are made of plastic, and accordingly, have a certain flexibility. During installation, the support frames 156 are connected with the sealed cabin 16 only through inserting the assembly bumps 161 into the assembly holes 1561 respectively for completing the fixation. During the design process, it is necessary to reserve a certain space for the insect collecting pipe 13, so a length of the support frames 156 is larger than a length of the insect collecting pipe 13, and preferably, the length of the support frames 156 is equal to the length of the insect collecting pipe 13 plus a length of the first entrances 131.

The camera 121 is set at a bottom of the circuit board 12 and is opposite to the insect collecting pipe 13. In order to ensure the normal shooting of the camera 121, a top of the insect collecting pipe 13 has an opening, the insect collecting pipe 13 is set vertically, the pests entering the insect collecting pipe 13 fall naturally to the bottom of the insect collecting pipe 13 under the action of gravity, so that there is no need to worry about the pests being discharged from the top of the insect collecting pipe 13, and moreover, the gap between the top of the insect collecting pipe 13 and the sealed cabin 16 is not too large, which is also able to effectively prevent the pests from climbing out.

A bottom surface of the sealed cabin 16 is made from transparent materials for ensuring that the camera 121 works normally, and preferably, the bottom surface of the sealed cabin 16 is made from transparent plastics. The camera 121 is set within the sealed cabin 16 for preventing the corrosive gas in the grain from damaging the camera 121.

To further seal the circuit board 12 within the sealed cabin 16, a sealing plug 17 is provided above the circuit board 12. The sealing plug 17 has reserved holes for allowing pins of the temperature sensor and the humidity sensor to pass through. Sealant is also coated on the sealing plug 17 for further sealing.

Fifth Embodiment

The fifth embodiment is a further improvement to the third embodiment, and the same components are not repeated here. Referring to FIGS. 1-7, a circular insect leaking passage 152 is provided outside the mounting hole 151. A round baffle 137 is provided on the insect collecting pipe 13 through a bracket 136 at a position corresponding to the circular insect leaking passage 152. The round baffle 137 has the same size as the insect leaking passage 152. The connecting rod 132 is provided at a center of the round baffle 137. The lower end of the insect collecting pipe 13 that is not covered by the round baffle 137 defines the third insect leaking hole 133. An upper portion of the insect leaking passage 152 is inclined to facilitate the pests to slide out. The bracket 136 and the round baffle 137 are able to increase an area of the third insect leaking hole 133 to the greatest extent, so as to achieve the effect of quick cleaning. The upper portion of the insect leaking passage 152 is inclined, so that the insects are able to slide down directly to the first insect leaking holes 153 under the action of gravity, thus the cleaning is done more cleanly.

Sixth Embodiment

Figure 8:
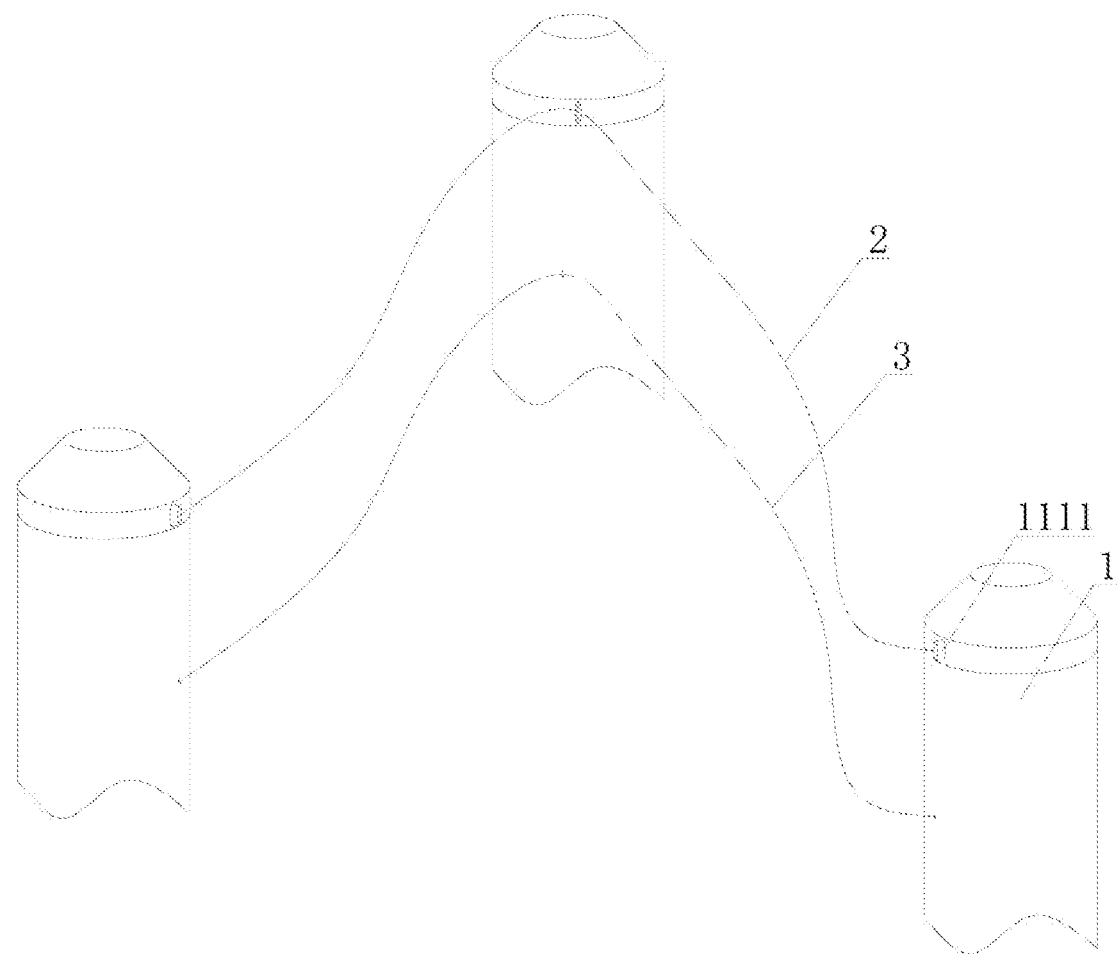
FIG. 8 shows a connection relationship among multiple easy-to-clean visual grain monitoring devices.

The sixth embodiment is a further improvement to the third embodiment, and the same components are not repeated here. Referring to FIG. 8, the easy-to-clean visual grain monitoring device 1 further comprises a cable unit, wherein the cable unit comprises a steel cable 2 for withstanding external forces and a signal wire 3 for signal transmission. The cable unit is introduced from an upper end of the housing 11 and leads out from a lower end of the housing 11. Each of the two support frames 156 has a cable trough for allowing the signal wire 3 to pass through. The cable unit is introduced into the housing 11 through a connecting hole 1112 of an end plug 111 on the upper end of the housing 11, wherein the steel cable 2 is connected with one of the two location pins 1111, preferably by winding for achieving the connection between the cable unit and the housing 11; the signal wire 3 is introduced into the housing 11, passes through the sealing plug 17 and is connected with the circuit board 12. Two end of the signal wire 3 exposed outside the housing 11 are connected with a peripheral processing device for real-time monitoring.

Seventh Embodiment

The seventh embodiment is a further improvement to the sixth embodiment, and the same components are not repeated here. Referring to FIGS. 1-6, a wireless transmission module, which is provided within the circuit board 12, sends wireless signals to the peripheral processing device for real-time monitoring. The cable unit is only provided with a steel cable for withstanding the external forces. The steel cable is connected with one location pin 1111 which is located at the upper end of the housing 11.

Eight Embodiment

A monitoring system which comprises the easy-to-clean visual grain monitoring device mentioned in the sixth embodiment of the present invention is illustrated. The monitoring system comprises multiple easy-to-clean visual grain monitoring devices connected with each other through multiple cable units. Every two adjacent visual grain monitoring devices are connected with each other through one cable unit, wherein two ends of the steel cable of the one cable unit are connected with a location pin 1111 which is located at a lower end of a housing 11 of an upper one of the two adjacent visual grain monitoring devices, and a location pin 1111 which is located at an upper end of a housing 11 of a lower one of the two adjacent visual grain monitoring devices; the signal wire of the one cable unit passes through a cable trough, and leads out from a connecting hole 1112 of an end plug 111 which is provided at the lower end of the housing 11 of the upper one of the two adjacent visual grain monitoring devices, and then enters the lower one of the two adjacent visual grain monitoring devices, and so on, thereby obtaining the monitoring system. In this way, monitoring systems with different lengths are able to be selected according to the needs of customers and the corresponding use environment. The length of the monitoring system depends on the gap between the two adjacent visual grain monitoring devices and the total number of the monitoring devices. When the monitoring system is placed, the grain sampling rod of the grain sampling machine is firstly inserted into the grain at a preset depth (which is able to be any depth in the granary), then the monitoring system is put into the grain sampling rod, and finally the grain sampling rod is taken out, so that the monitoring system is left in the grain for real-time monitoring.

Ninth Embodiment

A monitoring system which comprises the easy-to-clean visual grain monitoring device mentioned in the seventh embodiment of the present invention is illustrated. The monitoring system comprises multiple easy-to-clean visual grain monitoring devices connected with each other through multiple cable units. Every two adjacent visual grain monitoring devices are connected with each other through one cable unit, wherein two ends of a steel cable of the one cable unit are connected with a location pin 1111 which is located at a lower end of a housing 11 of an upper one of the two adjacent visual grain monitoring devices, and a location pin 1111 which is located at an upper end of a housing 11 of a lower one of the two adjacent visual grain monitoring devices respectively. The signals are sent by a wireless transmission module, which is provided within the circuit board 12 for signal transmission, and then are received by the external processing device, so that the connection without signal wires between the monitoring devices is able to be realized, which completely avoids the signal wire breakage due to pulling during the placement and removal of the monitoring system, thus affecting the signal transmission.

The above-mentioned embodiments only represent specific implementations of the present application, and the descriptions thereof are specific and detailed, but should not be construed as the limitation to the protection scope of the present application. It should be pointed out that for those skilled in the art, without departing from the technical solution of the present application, any modifications and improvements to the above-mentioned embodiments fall within the protection scope of the present application.

What is claimed is:

1. An easy-to-clean visual grain monitoring device, comprising a housing, wherein:
   a circuit board is provided within the housing and is connected with a monitoring unit;
   an insect collecting pipe, which is provided within the housing, comprises multiple first entrances;
   the housing comprises multiple second entrances which are corresponding to the first entrances respectively;
   an execution element, which is installed on a base, is connected with a lower end of the insect collecting pipe for driving the insect collecting pipe to move up and down;
   an insect leaking passage, which is provided at an upper end of the base, extends downwards along a side wall of the base;
   a tail end of the insect leaking passage has a first insect leaking hole for discharging pests, the housing has a second insect leaking hole in a position corresponding to the first insect leaking hole, and the lower end of the insect collecting pipe has a third insect leaking hole staggered with the insect leaking passage, wherein an upper end and a lower end of the housing has two openings respectively, two end plugs are provided at the upper and lower ends of the housing for sealing and are connected with the housing through two location pins respectively; the two end plugs have two connecting holes respectively; the monitoring unit comprises a camera, a temperature sensor and a humidity sensor; a fill-in light is provided beside the camera; the insect collecting pipe is provided at an area which is illuminated by the camera,
   wherein the execution element is installed on the base; a connecting rod, which is provided at the lower end of the insect collecting pipe near the base, is connected with an output end of the execution element; one end of the base near the insect collecting pipe has a mounting hole; the connecting rod and the output end of the execution element define a whole which is able to slide within the mounting hole, wherein the insect leaking passage, which is provided outside the mounting hole, extends downwards along the side wall of the base; the tail end of the insect leaking passage has the first insect leaking hole for discharging the pests; the housing has the second insect leaking hole in the position corresponding to the first insect leaking hole; the lower end of the insect collecting pipe has the third insect leaking hole staggered with the insect leaking passage; when the lower end of the insect collecting pipe is completely fitted with the base, the third insect leaking hole is blocked by the base, and at this time, the lower end of the insect collecting pipe and the base form a complete bottom surface, the insect leaking passage is blocked; when the execution element drives the insect collecting pipe to move upwards, the lower end of the insect collecting pipe is away from the base, so that a gap is formed between the insect collecting pipe and the base; and at the same time, the insect leaking passage is unblocked, the third insect leaking hole is unblocked.

2. The easy-to-clean visual grain monitoring device according to claim 1, wherein the base has a mounting slot for accommodating the execution element; a movement slot for accommodating the output end of the execution element is provided above the mounting slot; the mounting hole is provided above the movement slot; the connecting rod passes through the mounting hole and is connected with the output end of the execution element.

3. The easy-to-clean visual grain monitoring device according to claim 2, wherein two insect leaking passages are provided at two sides of the mounting hole, an upper end of the insect leaking passages and the mounting hole define a cuboid space; a strip, which matches the cuboid space, is provided at the lower end of the insect collecting pipe and is connected with the connecting rod; the third insect leaking hole is provided at the lower end of the insect collecting pipe where is not blocked by the strip.

4. The easy-to-clean visual grain monitoring device according to claim 3, wherein
   two first insect leaking holes are defined by two wedge-shaped grooves at two sides of the base and the housing sleeved on the base respectively; two head ends of the wedge-shaped grooves are communicated with the insect leaking passages, and two pointed ends of the wedge-shaped grooves are aligned with the second insect leaking holes respectively.

5. The easy-to-clean visual grain monitoring device according to claim 1, wherein
   a circular insect leaking passage is provided outside the mounting hole; a round baffle is provided on the insect collecting pipe through a bracket at a position corresponding to the circular insect leaking passage; the round baffle has the same size as the insect leaking passage; the connecting rod is provided at a center of the round baffle; the lower end of the insect collecting pipe that is not covered by the round baffle defines the third insect leaking hole; an upper portion of the insect leaking passage is inclined.

6. The easy-to-clean visual grain monitoring device according to claim 3, wherein the insect collecting pipe has two sliding slots at two sides thereof for limiting position, two support frames for cooperating with the sliding slots are provided on the base, and the support frames are engaged with the sliding slots respectively.

7. The easy-to-clean visual grain monitoring device according to claim 6, wherein
a sealed cabin is sleeved on the circuit board for sealing, two assembly bumps for connecting with the support frames respectively are provided at a lower portion of the sealed cabin, the two support frames have two assembly holes at an upper portion thereof respectively for cooperating with the two assembly bumps, the support frames are connected with the sealed cabin through inserting the assembly bumps into the assembly holes respectively, a length of the support frames is larger than a length of the insect collecting pipe.

8. The easy-to-clean visual grain monitoring device according to claim 7, wherein the camera is set at a bottom of the circuit board and is opposite to the insect collecting pipe, a bottom surface of the sealed cabin is made from transparent materials; a sealing plug is provided above the circuit board and within the sealed cabin, and has reserved holes for allowing pins of the temperature sensor and the humidity sensor to pass through.

9. A monitoring system with the easy-to-clean visual grain monitoring devices according to claim 8, the monitoring system comprising the easy-to-clean visual grain monitoring devices connected with each other through multiple cable units, wherein each of the cable units comprises a steel cable for withstanding external forces and a signal wire for signal transmission; two ends of the steel cable of the each of the cable units are connected with a location pin which is located at a lower end of a housing of an upper one of two adjacent visual grain monitoring devices, and a location pin which is located at an upper end of a housing of a lower one of the two adjacent visual grain monitoring devices, respectively.

* * * * *